(12) United States Patent
Ye et al.

(10) Patent No.: US 10,988,996 B2
(45) Date of Patent: Apr. 27, 2021

(54) APPLICATION OF ELECTRO-RHEOLOGY IN MEASUREMENTS OF DRILLING FLUID COMPOSITION

(71) Applicant: Halliburton Energy Services, Inc., Houston, TX (US)

(72) Inventors: Xiangnan Ye, Cypress, TX (US); Dale E. Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 66 days.

(21) Appl. No.: 16/479,569

(22) PCT Filed: Dec. 21, 2017

(86) PCT No.: PCT/US2017/067952
§ 371 (c)(1),
(2) Date: Jul. 19, 2019

(87) PCT Pub. No.: WO2019/125471
PCT Pub. Date: Jun. 27, 2019

(65) Prior Publication Data
US 2019/0360286 A1    Nov. 28, 2019

(51) Int. Cl.
*E21B 21/06* (2006.01)
*E21B 49/08* (2006.01)
*G16C 20/30* (2019.01)

(52) U.S. Cl.
CPC ............ *E21B 21/06* (2013.01); *E21B 49/087* (2013.01); *G16C 20/30* (2019.02)

(58) Field of Classification Search
CPC ....... E21B 21/06; E21B 49/087; G16C 20/30; G01N 2011/0066; G01N 11/00
See application file for complete search history.

(56) References Cited

U.S. PATENT DOCUMENTS 3,294,184 A * 12/1966 O'Brien .................. C09K 8/02
175/65
6,719,055 B2 * 4/2004 Mese ....................... C09K 8/32
166/308.1
(Continued)

FOREIGN PATENT DOCUMENTS

CA          2535531         2/2005
WO        2015050120        9/2015
(Continued)

OTHER PUBLICATIONS

ISRWO International Search Report and Written Opinion for PCT/US2017/067952 dated Sep. 21, 2018.
Anton Paar, MCR, The Modular Compact Rheometer Series, 2016.

*Primary Examiner* — Taras P Bemko
*Assistant Examiner* — Yanick A Akaragwe
(74) *Attorney, Agent, or Firm* — Tenley Krueger; C. Tumey Law Group PLLC

(57) ABSTRACT

Systems and methods for determining the composition of a drilling fluid using electro-rheology may be provided. A method for drilling a wellbore may include circulating a drilling fluid in a wellbore. The method may include extending the wellbore into one or more subterranean formations. The method may include measuring one or more rheological properties of at least a portion of the drilling fluid while applying an electric field to the drilling fluid to obtain an electro-rheological profile of the portion of the drilling fluid. The method may include determining an estimate of a concentration of at least one additive of the drilling fluid based on the electro-rheological profile.

20 Claims, 10 Drawing Sheets

(56) References Cited

U.S. PATENT DOCUMENTS

| | | |
|---|---|---|
| 2003/0136560 A1 | 7/2003 | Mese et al. |
| 2004/0168811 A1 | 9/2004 | Shaw et al. |
| 2009/0163386 A1* | 6/2009 | Dino ............... C09K 8/36 |
| | | 507/103 |
| 2011/0161010 A1 | 6/2011 | Rickman |
| 2014/0224480 A1 | 8/2014 | Nguyen et al. |
| 2016/0216187 A1* | 7/2016 | Gao ............... G01N 11/00 |
| 2016/0216190 A1 | 7/2016 | Palla et al. |
| 2017/0131226 A1 | 5/2017 | Boul et al. |
| 2017/0198189 A1* | 7/2017 | Panamarathupalayam ........... |
| | | E21B 21/003 |

FOREIGN PATENT DOCUMENTS

| | | |
|---|---|---|
| WO | 2017040158 | 3/2017 |
| WO | 2018038717 | 3/2018 |

* cited by examiner

APPLICATION OF ELECTRO-RHEOLOGY IN MEASUREMENTS OF DRILLING FLUID COMPOSITION

BACKGROUND

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, emulsifying surfactants, and the like), and combinations thereof, to impart certain properties to the drilling fluid to satisfy different drilling requirements.

The drilling fluid can serve several functions, one of them being to transport wellbore cuttings up to the surface where they are separated from the drilling fluid. Another function of the drilling fluid can include providing hydrostatic pressure against the wall of the drilled wellbore, thereby preventing wellbore collapse and the resulting influx of gas or liquid from the formations being penetrated. For these and other reasons, it can be important to know the characteristics and chemical composition of the drilling fluid during circulation.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

DETAILED DESCRIPTION

Figure 1:
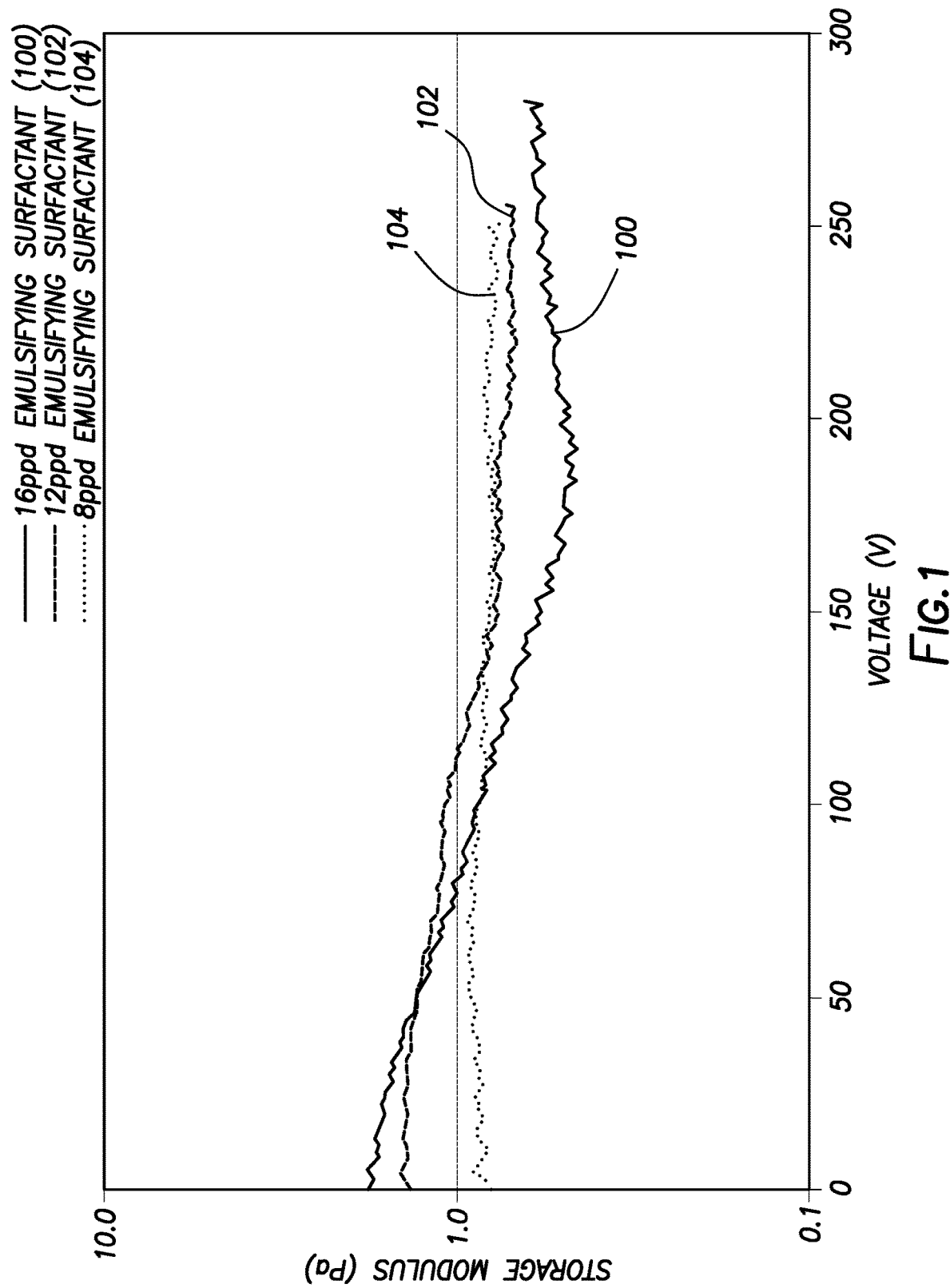
FIG. 1 illustrates a plot of measured storage modulus as a function of applied voltage for three drilling fluids with different emulsifier concentrations.

The present disclosure relates to drilling operations and, more particularly, embodiments disclosed herein are directed to systems and methods for determining the composition of a drilling fluid using electro-rheology. By way of example, electro-rheology may be used to determine an estimate of the concentration of one or more components of a drilling fluid. Electro-rheology typically refers to modifying the rheology of fluids by application of an electric field. Because the rheology of the drilling fluid may be dependent on the applied electric field, electro-rheology may be used to determine the composition of the drilling fluid. In particular, rheology measurements may be taken while the electric field is applied. One or more of the components of the drilling fluid may impact rheology, which may be more pronounced under an electric field, as the one or more components may be responsive to the electric fields. Thus, rheology measurement taken under application of the electric field can be used to determine the composition of the drilling fluid.

The drilling fluid may include hydrocarbon-based drilling fluids, which may include a hydrocarbon liquid as the base fluid, which may be synthetic or oil-based. The drilling fluid may include invert emulsion, which may include an external phase and an internal phase. The external phase may include a hydrocarbon liquid. The external phase can include dissolved materials or undissolved solids. Any suitable hydrocarbon liquid may be used in the external phase, including, but not limited to, a fractional distillate of crude oil; a fatty derivative of an acid, an ester, an ether, an alcohol, an amine, an amide, or an imide; a saturated hydrocarbon; an unsaturated hydrocarbon; a branched hydrocarbon; a cyclic hydrocarbon; and any combination thereof. Crude oil can be separated into fractional distillates based on the boiling point of the fractions in the crude oil. An example of a suitable fractional distillate of crude oil is diesel oil. The saturated hydrocarbon can be an alkane or paraffin. For example, the saturated hydrocarbon may be an isoalkane, a linear alkane, or a cyclic alkane. Examples of suitable saturated hydrocarbons may include a combination of an isoalkane and an n-alkane or a mineral oil blend that includes alkanes and cyclic alkanes. The unsaturated hydrocarbon may include an alkene, alkyne, or aromatic. The alkene may include an isoalkane, linear alkene, or cyclic alkene. The linear alkene may include a linear alpha olefin or an internal olefin. The hydrocarbon liquid may be present in the drilling fluid in an any suitable amount, including an amount ranging from about 1 wt. % to about 90 wt. % based on a total weight of the drilling fluid. For example, the hydrocarbon liquid may be present in the drilling fluid in an amount of about 10 wt. %, about 20 wt. %, about 30 wt. %, about 40 wt. %, about 50 wt. %, about 60 wt. %, about 70 wt. %, about 80 wt. %, or about 90 wt. %, based on a total weight of the drilling fluid. One of ordinary skill in the art with the benefit of this disclosure should recognize the appropriate amount of the aqueous liquid for a chosen application.

The internal phase may include an aqueous liquid. The aqueous liquid may be from any source provided that it does not contain an excess of compounds that may undesirably affect other components in the drilling fluids. For example, a drilling fluid may include fresh water or salt water. Salt water generally may include one or more dissolved salts therein and may be saturated or unsaturated as desired for a particular application. Seawater or brines may be suitable for use in some examples. The aqueous liquid may be present in the drilling fluid in an any suitable amount, including an amount ranging from about 1 wt. % to about 90 wt. % based on a total weight of the drilling fluid. For example, the aqueous liquid may be present in the drilling fluid in an amount of about 10 wt. %, about 20 wt. %, about 30 wt. %, about 40 wt. %, about 50 wt. %, about 60 wt. %, about 70 wt. %, about 80 wt. %, or about 90 wt. %, based on a total weight of the drilling fluid. One of ordinary skill in the art with the benefit of this disclosure should recognize the appropriate amount of the aqueous liquid for a chosen application.

As previously described, one or more dissolved salts may also be present in the aqueous liquid. Where used, the dissolved salt may be included in the aqueous liquid for any purpose, including, but not limited to, densifying a drilling fluid including water to a chosen density. A mixture of one or more dissolved salts and water may be used in some instances. The amount of salt that should be added may be the amount needed to provide a desired density. One or more salts may be added to the water to provide a brine that includes the dissolved salt and the water. Suitable dissolved salts may include monovalent (group I) and divalent salts (group II). Mixtures of monovalent, divalent, and trivalent salts may also be used. Suitable salts may include, but are not limited to, sodium chloride, calcium chloride, sodium bromide, potassium bromide, potassium chloride, potassium formate, cesium formate, lithium chloride, lithium bromide sodium formate, lithium formate, ammonium chloride, organic cation salts such as tetramethyl ammonium chloride, choline chloride, and mixtures thereof among others. The salt may be provided in any amount or concentration such as unsaturated, saturated, supersaturated, and saturated with additional solids. For example, the salt may be provided in an amount in a range of about 1 wt. % to about 40 wt. % based on a total weight of the aqueous liquid. Alternatively, the salt may be present in the drilling fluid in an amount of about 1 wt. %, about 10 wt. %, about 20 wt. %, about 30 wt. %, or about 40 wt. % based on a total weight of the drilling fluid. One of ordinary skill in the art with the benefit of this disclosure should recognize the appropriate amount of the salt for a chosen application.

The drilling fluids may include an emulsifying surfactant. Emulsifying surfactants may include, without limitation, fatty amines, ethoxylated nonylphenols, fatty acids, fatty acid esters, and combinations thereof. In general, suitable emulsifying surfactants may have a Griffin's HLB (hydrophilic-lipophilic balance) of about 9 or greater may be suitable used. Fatty acids and fatty acid esters may be of particular interest as they are generally non-hazardous to the working environment and may pose little environmental risk. The Griffin's HLB values may be calculated by the following formula:

$$HLB = 20 * \frac{M_h}{M}$$

where $M_h$ is the molecular mass of the hydrophilic portion of the molecule and M is the molecular mass of the whole molecule. One of ordinary skill in the art with the benefit of this disclosure should be able to determine if a particular emulsifying surfactant includes a Griffin's HLB value of greater than about 9.

One of ordinary skill will appreciate that the emulsifying surfactants may be present in any amount suitable for a particular application. In some examples, without limitation, the emulsifying surfactant may be present in the drilling fluid in an amount ranging from about 0.5 wt. % to about 10 wt. % based on a total weight of the drilling fluid. Specific amounts of the emulsifying surfactant may include, but are not limited to about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, or about 10 wt. % based on a total weight of the drilling fluid. One of ordinary skill in the art with the benefit of this disclosure should recognize the appropriate amount of the emulsifying surfactant for a chosen application.

The drilling fluids may include a clay. Any of a variety of different clays may be included in the drilling fluids. Suitable clays may include, but are not limited to, sepiolite, attapulgite, calcium bentonite, sodium bentonite, calcium montromillonite, organoclays, and combinations thereof. Organoclays are organically modified phyllosilicate formed by exchanging interlayer cations for alkylammonium or phosphonium ions. The clay may be present in any suitable amount for a particular application, including, but not limited to, an amount ranging from about 1 wt. % to about 50 wt. % based on a total weight of the drilling fluid. For example, the clay may be present in an amount of about 1 wt %, about 10 wt. %, about 20 wt. %, about 30% wt. %, about 40 wt. %, or about 50 wt. % based on a total weight of the drilling fluid.

A wide variety of additional additives may be included in the drilling fluids as desired for a particular application. Suitable additives may include, but are not limited to, viscosifiers, shale stabilizers, wetting agents, and weighting agents, among others. Suitable viscosifiers may include, but are not limited to, water soluble starches and modified versions thereof, water-soluble polysaccharides and modified versions thereof, water soluble celluloses and modified versions thereof, water soluble polyacrylamides and copolymers thereof, biopolymers, and combinations thereof. One of ordinary skill, with the benefit of this disclosure, should be able to select additional drilling fluid additives for a particular application.

Those of ordinary skill in the art will appreciate that the drilling fluid generally should have a density suitable for a particular application. By way of example, the drilling fluid may have a density in the range of from about 7 pounds per gallon ("lb/gal") (838.8 kg/m$^3$) to about 20 lb/gal (2397 kg/m$^3$). In certain embodiments, the drilling fluid may have a density in the range of from about 8 lb/gal (958.6 kg/m$^3$) to about 12 lb/gal (1438 kg/m$^3$). Those of ordinary skill in the art, with the benefit of this disclosure, should recognize the appropriate density for a particular application.

When drilling a wellbore, the drilling fluid may be continuously circulated from the well surface down to the bottom of the wellbore being drilled and back to the well surface again. The composition of the drilling fluid may change during the course of the drilling fluid due to a number of factors, including, but not limited to, the loss of drilling fluid additives in the wellbore and the addition of drill solids into the drilling fluid. To maintain adequate properties of the drilling fluid, the drilling fluid may be monitored to determine its composition at the surface while it is being circulated.

The methods and systems disclosed may use electro-rheology to determine an estimate of the concentration of one or more components of a drilling fluid. Because certain components, such as clays and emulsifying surfactants, are responsive to applied electric fields, their impact on rheology will be more pronounced under the electric field, electro-rheology may be used to determine an estimate of their concentration. In particular, these components, such as the clays and emulsifying surfactants, may be non-conducting, but electrically active. Remedial action may be taken if the concentration is below a predetermined threshold. For example, an additional quantity of the additive may be added to the drilling fluid to increase the concentration of the additive. Prior to performing electro-rheology measurements on the drilling fluid from a wellsite, tests may initially be performed to determine the effective the electric field on the rheology of sample drilling fluids having known compositions. By way of example, electro-rheology measurements may be performed on the sample drilling fluids. From the measurements, rheological properties of the sample drilling fluids may be determined. The rheological properties may include, but are not limited to, storage modulus, loss modulus, viscosity, shear viscosity, dynamic viscosity, shear stress, shear modulus, yield stress, among others. The rheological properties may be plotted as a function of electric field properties, such as voltage or current. A correlation may then be established between a concentration of a drilling fluid additive and the rheological property. Based on this correlation, the concentration of the drilling fluid circulating at the well site may be determined. It has been determined that storage modulus from electro-rheology may be strongly dependent upon concentration of emulsifying surfactant, allowing use of storage modulus in development of the correlation. In addition, due to this dependent, storage modulus may also be used to determine the type of hydrocarbon liquid in a drilling fluid.

Sample techniques for determining this correlation will now be described with respect to FIGS. 1-5. FIG. 1 is a plot of storage modulus versus voltage of an example in which electro-rheology measurements were performed for three sample drilling fluids having varying concentrations of an emulsifying surfactant. The electro-rheology measurements for the example of FIG. 1 were performed by applying an electric field to the sample drilling fluids in a rheometer. The rheometer was an Anton Paar MCR 501 Rheometer that included two parallel plates with a diameter of 1 inch (25 mm) and a gap of 0.04 inches (1 mm) between which the sample drilling fluids were disposed. In this example, a direct current electric field was applied between the two parallel plates and increased linearly at a rate of 1.67 volts per second. While the electric field was applied, the top plate was oscillated while the bottom plate was stationary. The emulsifying surfactant used in the sample drilling fluids was a carboxylic acid terminated fatty polyamide. The hydrocarbon liquid used in the sample drilling fluids was a synthetic paraffin base oil, available from Halliburton Energy Services, Inc., as XP-07™ synthetic paraffin base oil. The weight ratio of oil to water the sample drilling fluid was 80:20. All three drilling fluids had a density of about 12 pounds per gallon (1437.92 kg/m$^3$).

The storage modulus as a function of voltage is shown in FIG. 1 for the three sample drilling fluids. Specifically, the curve 100 is representative of a drilling fluid that includes 16 pounds per barrel (46 kg/m$^3$) of an emulsifying surfactant. The curve 102 is representative of a drilling fluid that includes 12 pounds per barrel (34 kg/m$^3$) of an emulsifying surfactant. The curve 104 is representative of a drilling fluid that includes 8 pounds per barrel (23 kg/m$^3$) of an emulsifying surfactant. As illustrated by FIG. 1, the storage modulus as a function of voltage is generally constant with increasing voltage for the sample drilling fluid of curve 106 with 8 pounds per barrel (23 kg/m$^3$) of the emulsifying surfactant. However, increasing the concentration of the emulsifying surfactant, causes a decrease of the storage modulus when increasing the voltage of the electric field. The slope of the storage modulus as a function of voltage for each of the three sample drilling fluids may be obtained and plotted as a function of emulsifying surfactant concentration. A correlation may then be developed from this plot between storage modulus slope and emulsifying surfactant concentration.

Figure 2:
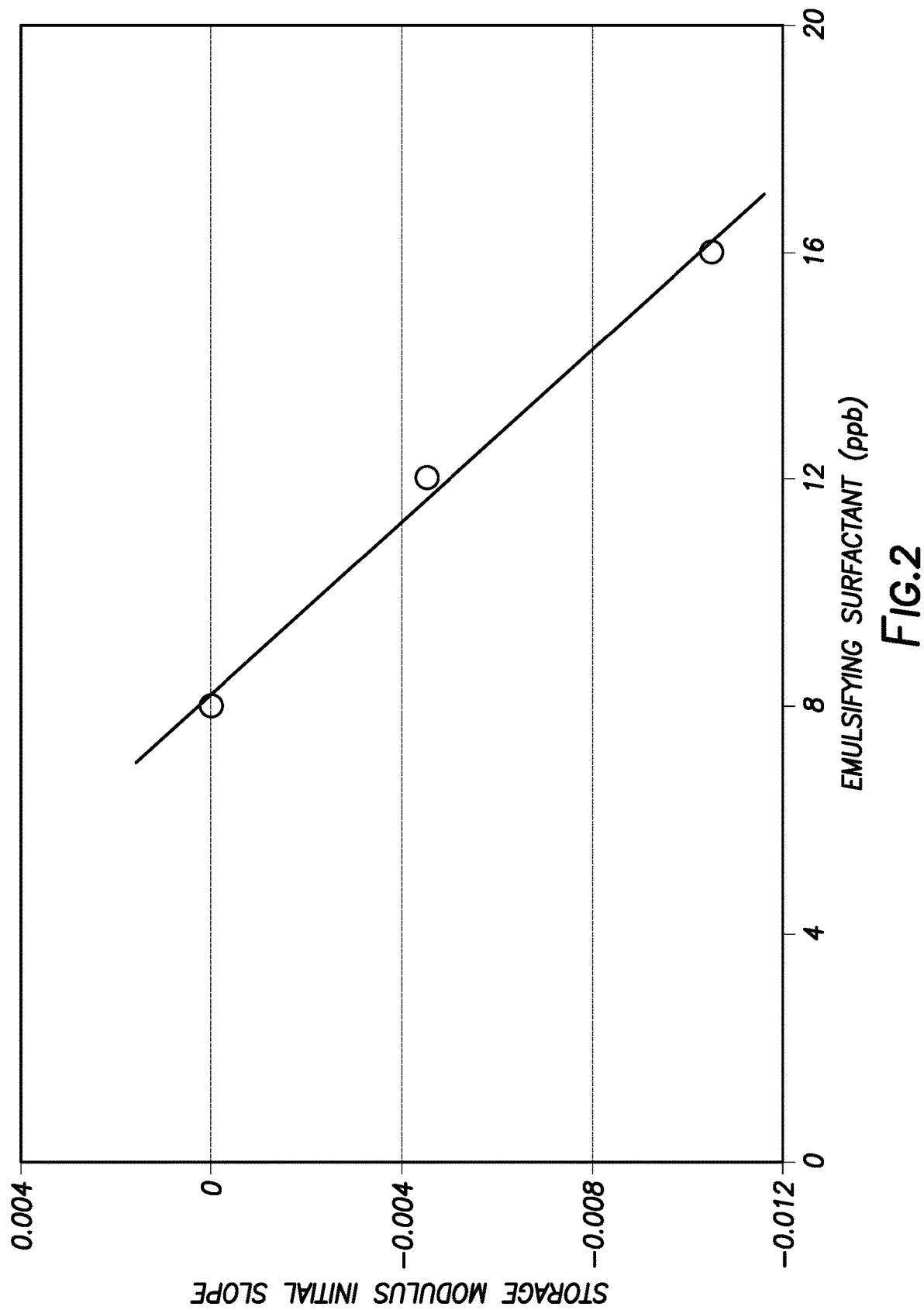
FIG. 2 illustrates a plot of storage modulus initial slope as a function of emulsifier concentration.

FIG. 2 is a plot of storage modulus initial slope versus emulsifying surfactant concentration. To obtain FIG. 2, the storage modulus initial slope is obtained from FIG. 1 between 0 volts to 100 volts and plotted as a function of emulsifying surfactant concentration. A correlation between the emulsifying surfactant concentration and the storage modulus initial slope may be obtained. For example, a linear relationship between emulsifying surfactant concentration and the storage modulus initial slope may be obtained with $Y=-1.31E-3*X+1.08E-2$. With this correlation, the amount of emulsifying surfactant may be obtained. By way of example, a drilling fluid with a similar base fluid to three sample drilling fluids may be used in a drilling a well. Electro-rheology measurements of the drilling fluid may be obtained, either continuously or intermittently, from which a storage modulus slope may be obtained. With the storage modulus slope, the correlation may be used to determine an estimate of the emulsifying surfactant concentration.

Figure 3:
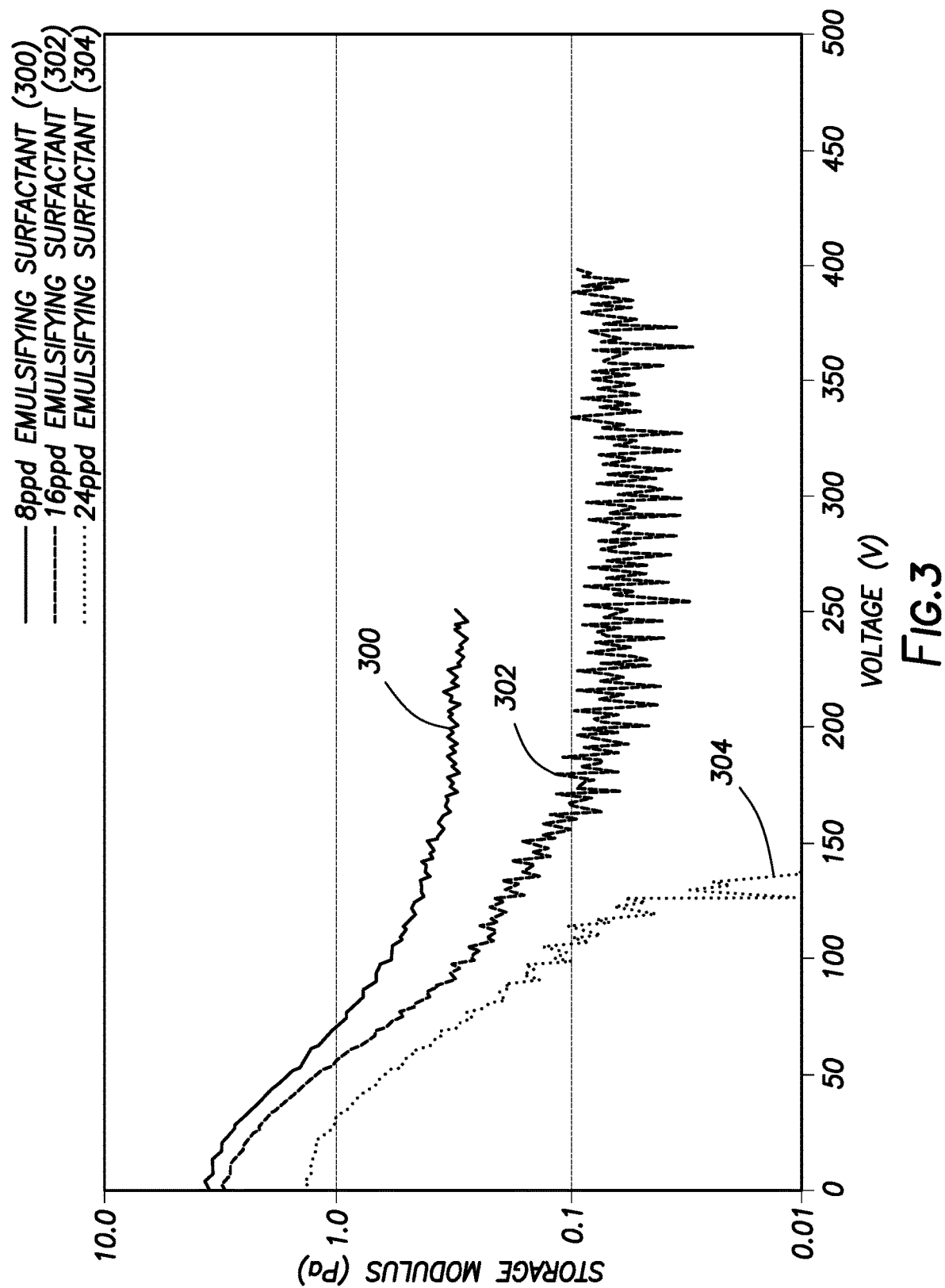
FIG. 3 illustrates a plot of storage modulus as a function of applied direct current voltage for three drilling fluids with different emulsifier concentrations.

FIG. 3 is a plot of storage modulus versus voltage of another example in which electro-rheology measurements were performed for three sample drilling fluids having varying concentrations of an emulsifying surfactant. The sample drilling fluids for this example used a different hydrocarbon liquid than the sample drilling fluids for the example of FIG. 1. The electro-rheology measurements for this example were performed as described above for the example of FIG. 1. The emulsifying surfactant used in the sample drilling fluids was a carboxylic acid terminated fatty polyamide with C16-C18 internal olefins. The hydrocarbon liquid used in the sample drilling fluids was a blend of esters and internal olefins, available from Halliburton Energy Services, Inc., as ACCOLADE® base. All three drilling fluids had a density of about 13 pounds per gallon (1557.74 kg/m$^3$).

The storage modulus as a function of voltage is shown in FIG. 3 for the three sample drilling fluids. Specifically, the curve 300 is representative of a drilling fluid that includes 8 pounds per barrel (23 kg/m$^3$) of an emulsifying surfactant. The curve 302 is representative of a drilling fluid that includes 12 pounds per barrel (34 kg/m$^3$) of an emulsifying surfactant. The curve 304 is representative of a drilling fluid that includes 16 pounds per barrel (46 kg/m$^3$) of an emulsifying surfactant. As illustrated by FIG. 3, the storage modulus as a function of voltage is strongly dependent upon concentration of the emulsifying surfactant. Accordingly, a correlation may then be developed from this plot between storage modulus slope and emulsifying surfactant concentration from which emulsifying surfactant concentration may be determined for a drilling fluid with electro-rheology.

While FIGS. 1-3 illustrate development of correlations for determining an estimate of emulsifying surfactant concentration, it should be understood that electro-rheology may be used to develop correlations for other drilling fluid additives that are responsive to electric fields. For example, correlations may be developed that can be used to determine clay concentration. Due to their polar nature, the clay in the drilling fluid may orient under an applied electric field.

Figure 4:
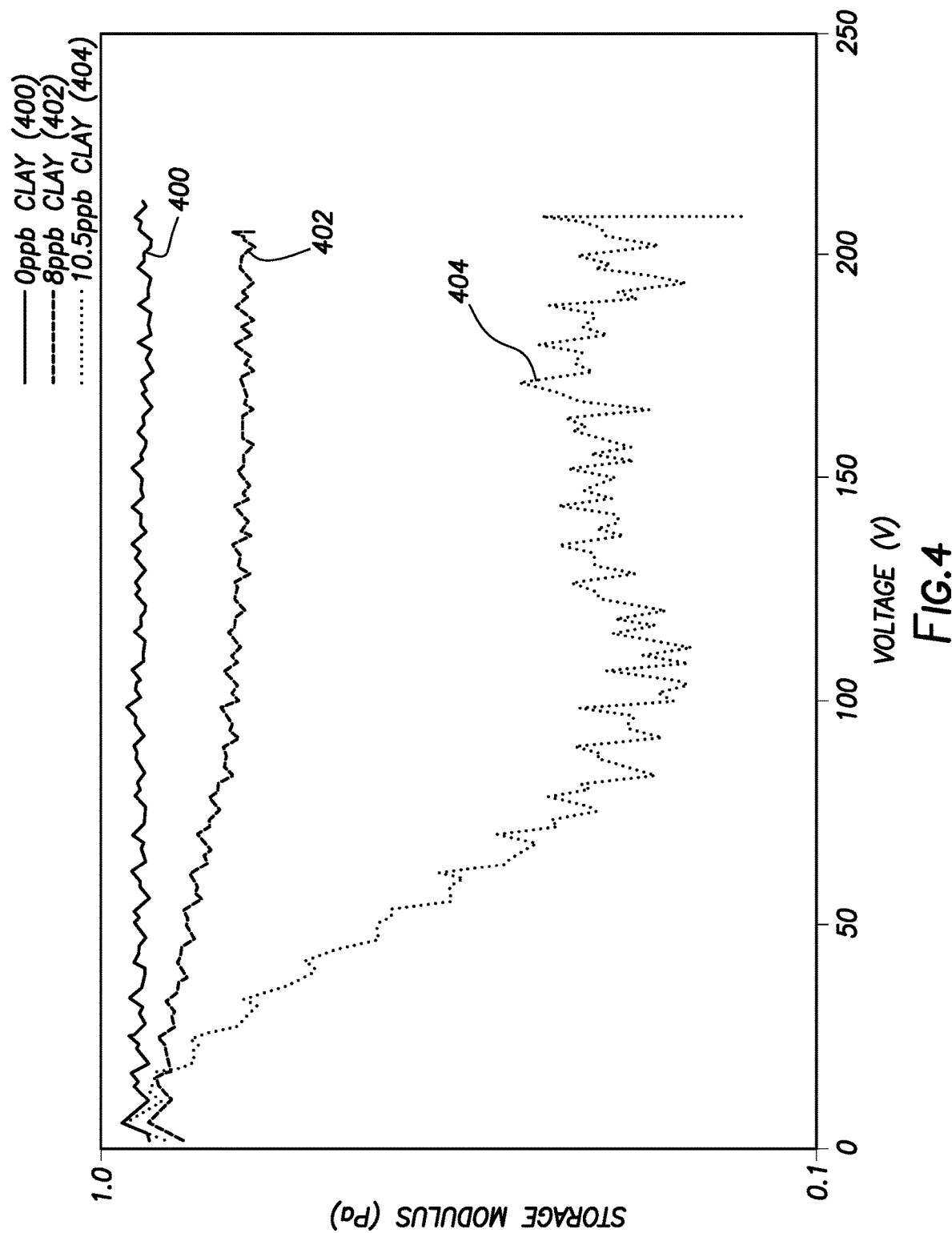
FIG. 4 illustrates a plot of storage modulus as a function of applied direct current voltage for three drilling fluids with different clay concentrations.

FIG. 4 is a plot of storage modulus versus voltage of an example in which electro-rheology measurements were performed for three sample drilling fluids having varying concentrations of clay. The electro-rheology measurements for this example were performed as described above for the example of FIG. 1. The clay used in the sample drilling fluids was an organophilic clay, available as GELTONE® emulsifier available from Halliburton Energy Services, Inc. The hydrocarbon liquid used in the sample drilling fluids was a synthetic paraffin base oil, available from Halliburton Energy Services, Inc., as XP-07™ synthetic paraffin base oil. The weight ratio of oil to water the sample drilling fluid was 70:30 All three drilling fluids had a density of about 7.8 pounds per gallon (934.65 kg/m$^3$).

The storage modulus as a function of voltage is shown in FIG. 4 for the three sample drilling fluids. Specifically, the curve 400 is representative of a drilling fluid that includes 0 pounds per barrel (0 kg/m$^3$) of the clay. The curve 402 is representative of a drilling fluid that includes 8 pounds per barrel (23 kg/m$^3$) of the clay. The curve 404 is representative of a drilling fluid that includes 10.5 pounds per barrel (30 kg/m$^3$) of the clay. As illustrated by FIG. 4, the storage modulus as a function of voltage is strongly dependent upon concentration of the clay. As the concentration of the clay in the sample drilling fluids increased, the drop in storage modulus as a function of voltage increased. Accordingly, a correlation may then be developed from this plot between storage modulus slope and clay concentration from which clay concentration may be determined for a drilling fluid with electro-rheology.

Figure 5:
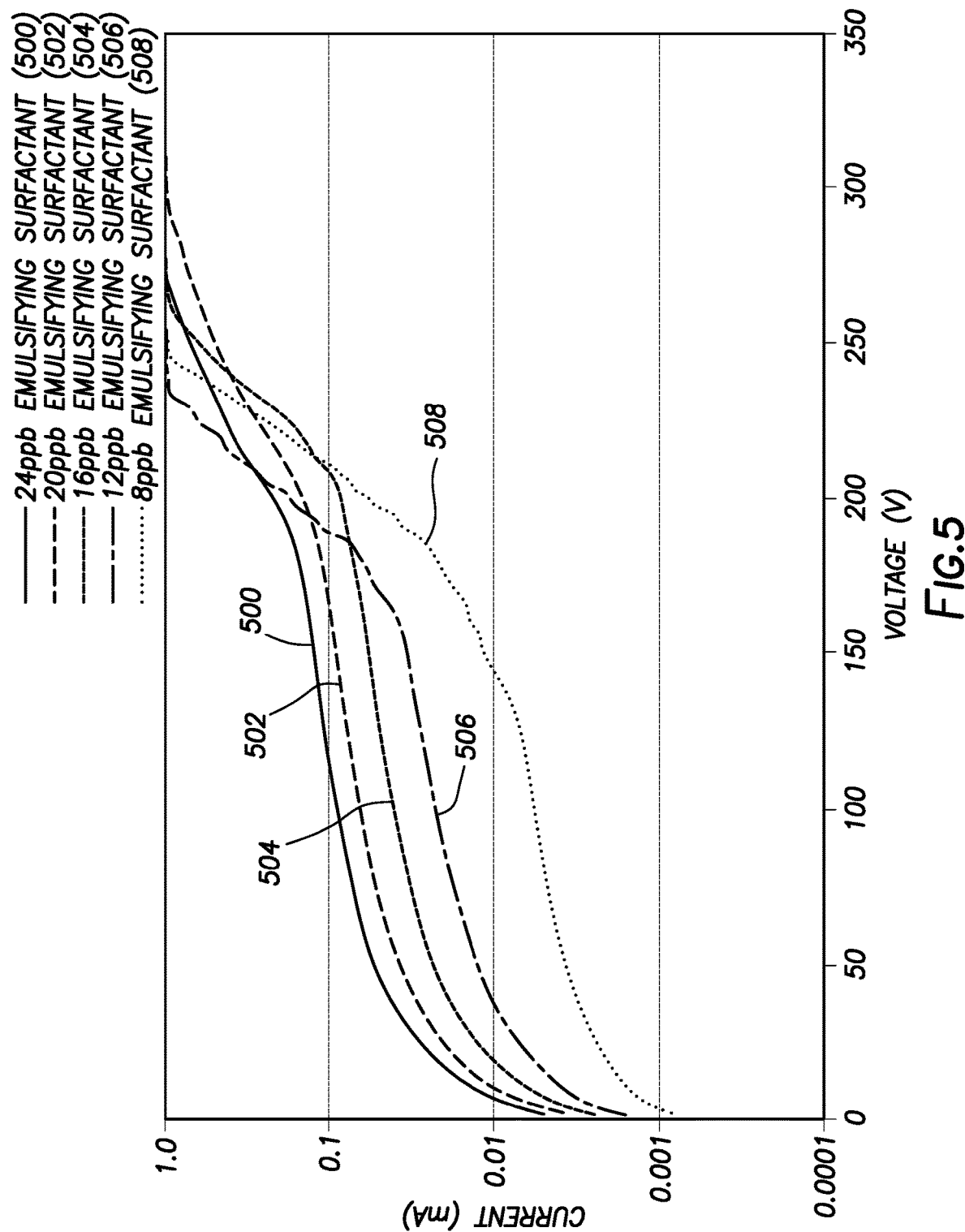
FIG. 5 illustrates a plot of current across a drilling fluid sample as a function of voltage.

While FIGS. 1-4 illustrate development of correlations using the voltage, other parameters of the electric field may be used to generate the correlation. FIG. 5 is a plot of current versus voltage of an example in which electro-rheology measurements were performed for five sample drilling fluids having varying concentrations of clay. The electro-rheology measurements for this example were performed as described above for the example of FIG. 1. The emulsifying surfactant used in the sample drilling fluids was a carboxylic acid terminated fatty polyamide. The hydrocarbon liquid used in the sample drilling fluids was a synthetic paraffin base oil, available from Halliburton Energy Services, Inc., as XP-07™ synthetic paraffin base oil. The weight ratio of oil to water the sample drilling fluid was 80:20. All five drilling fluids had a density of about 12 pounds per gallon (1437.92 kg/m$^3$).

Figure 10:
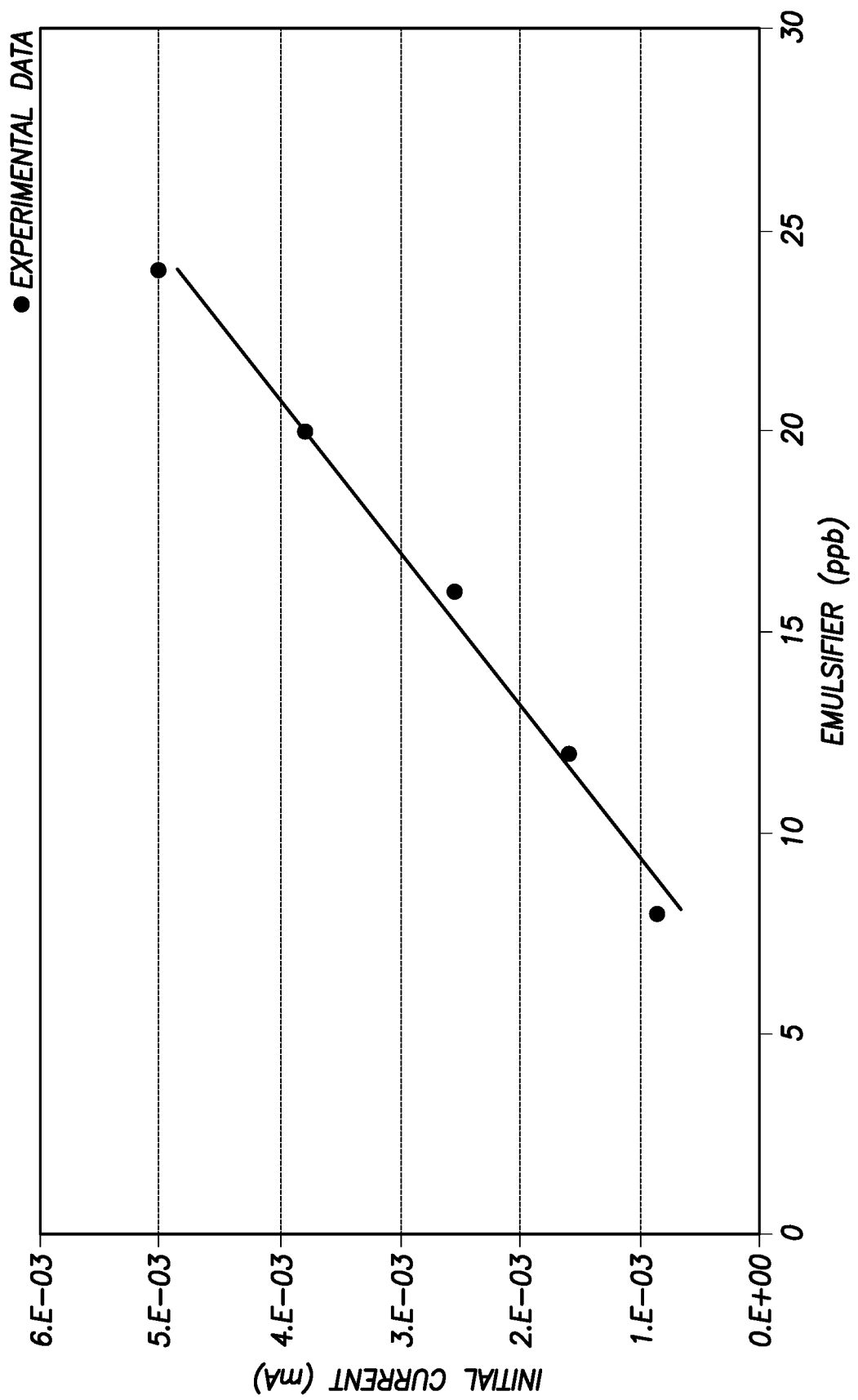
FIG. 10 illustrates a plot of current across a drilling fluid sample as a function of emulsifier concentration.

The current as a function of voltage is shown in FIG. 5 for the five sample drilling fluids. Specifically, the curve 500 is representative of a drilling fluid that includes 24 pounds per barrel (68 kg/m$^3$) of an emulsifying surfactant. Curve 502 is representative of a drilling fluid that includes 20 pounds per barrel (57 kg/m$^3$) of an emulsifying surfactant Curve 504 is representative of a drilling fluid that includes 16 pounds per barrel (46 kg/m$^3$) of an emulsifying surfactant. The curve 506 is representative of a drilling fluid that includes 12 pounds per barrel (34 kg/m$^3$) of an emulsifying surfactant. The curve 508 is representative of a drilling fluid that includes 8 pounds per barrel (23 kg/m$^3$) of an emulsifying surfactant. A correlation may then be developed using the experimental data on FIG. 5 to determine emulsifier concentration as a function of current. For example, taking the current at time=1 second as the initial current, the initial current as a function of emulsifier may be plotted as shown in FIG. 10. As illustrated on FIG. 10, a liner dependent may be shown between the initial current and emulsifier concentration as follows: Y=2.64E-4*X−1.47E-3.

Any of a variety of suitable rheological tests may be used with electro-rheology in development of the correlation. The preceding examples use oscillation deformation while increasing the voltage, for example, at 1.67 volts per seconds. However, the tests should not be limited to this particular voltage increase and any suitable voltage increase may be used, including, but not limited, a voltage increase at a rate ranging from 0.05 volts per second to 50 volts per second. The rate of voltage increase may be optimized, for example, based on the particular drilling fluid being tested. In addition, other suitable rheological tests may be used, including, but not limited to, simple shear, step relaxation, and creep flow, among others. In addition, while the preceding description described use of a parallel plate rheometer, the electro-rheology may be performed using other suitable rheometers, including, but not limited to, bob-and-cup rheometers.

Figure 6:
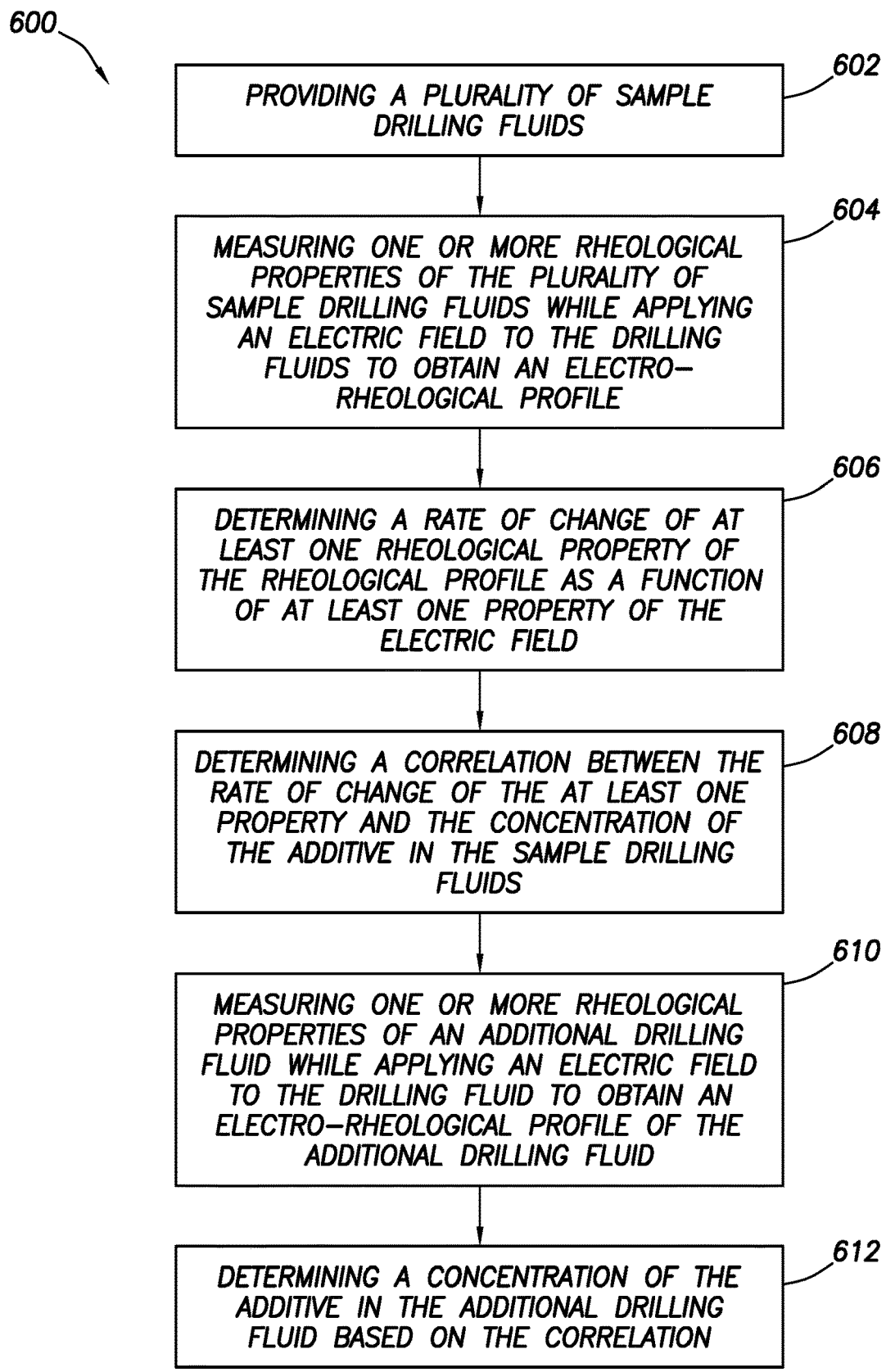
FIG. 6 illustrates a flow chart of an example method for using electro-rheology in determining drilling fluid properties.

FIG. 6 illustrates an flow chart of a method 600 of using electro-rheology in determining drilling fluid properties. In particular, the method 600 may be used to determine a concentration of an additive in a drilling fluid. The method 600 may include providing a plurality of sample drilling fluids, as shown at block 602. Each of the sample drilling fluids may include a hydrocarbon liquid, an aqueous liquid, and an additive, as previously described herein. For example, the sample drilling fluids may include an invert emulsions, wherein an external phase of invert emulsion including the hydrocarbon liquid and the internal phase of the invert emulsion includes the aqueous liquid. The concentration of the additive in each of the sample drilling fluids may be different. The sample drilling fluids may include two, three, four, five, or more sample drilling fluids.

At block 604, the method 600 may further include measuring one or more rheological properties of the plurality of sample drilling fluids while applying an electric field to obtain an electro-rheological profile for each of the sample drilling fluids. This measurement step in block 604 may be referred to as electro-rheology as the rheology of the sample drilling fluids is measured while applying an electric field. The electro-rheology profile refers to the rheological data obtained from the rheology measurements while applying an electric field, including one or more of the rheological properties and one or more of the electric field properties. This measurement may be performed individually for each of the sample drilling fluids. The rheological properties may include, but are not limited to, storage modulus, loss modulus, viscosity, and yield stress, among others. For example, the rheological profile may include one or more rheological properties as a function of voltage or current. The electric field may include application of direct current voltage. The direct current voltage may be varied while the measuring the one or more rheological properties. For example, the direct current voltage may be increased or decreased.

At block 606, the method 600 may further include determining a determining a rate of change of at least one rheological property of the rheological profile as a function of at least property of the electric field for each of the sample drilling fluids. The rate of change may include the rate of change of at least one rheological property as a function voltage. In one particular example, the rate of change may include the rate of change of storage modulus as a function of voltage, as described above. The rate of change may also include the rate of change of at least one rheological property as a function of current.

At block 608, the method 600 may further include determining a correlation between the rate of change of the at least one rheological property and the concentration of the additive in the sample drilling fluids. As previously described, the rate of change of the at least one rheological property (e.g., storage modulus, loss modulus, viscosity, and yield stress, etc.) and the concentration of the additive in the sample drilling fluids may have a linear relationship, for example, as shown on FIG. 2. This correlation may be used to determine concentration of the one or more additives in additional drilling fluids.

At block 610, the method 600 may further include measuring one or more rheological properties of an additional drilling fluid while applying an electric field to the drilling fluid to obtain an electro-rheological profile of the additional drilling fluid. The additional drilling fluid may be a sample drilling fluid prepare in a laboratory or a drilling fluid used at a wellsite, for example. The measurement may be performed at any suitable location, in a laboratory or at the wellsite, for example. The additional drilling fluid may include the hydrocarbon liquid, the aqueous liquid, and the additive, as previously described herein. For example, the additional drilling fluid may include an invert emulsion, wherein an external phase of invert emulsion including the hydrocarbon liquid and the internal phase of the invert emulsion includes the aqueous liquid. The concentration of the additive in the additional drilling fluid may not be known so that the correlation from block 608 may be used to determine its concentration.

At block 612, the method 600 may further include determining a concentration of the additive in the additional drilling fluid based on the correlation. The concentration may be determined by applying date from the electro-rheological profile of the additional drilling fluid to the correlation. For example, a rate of change may be determined for one or more of the rheological properties as a function of at least one property of the electric field for each of the sample drilling fluids. This rate of change may then be applied to the correlation.

Figure 7:
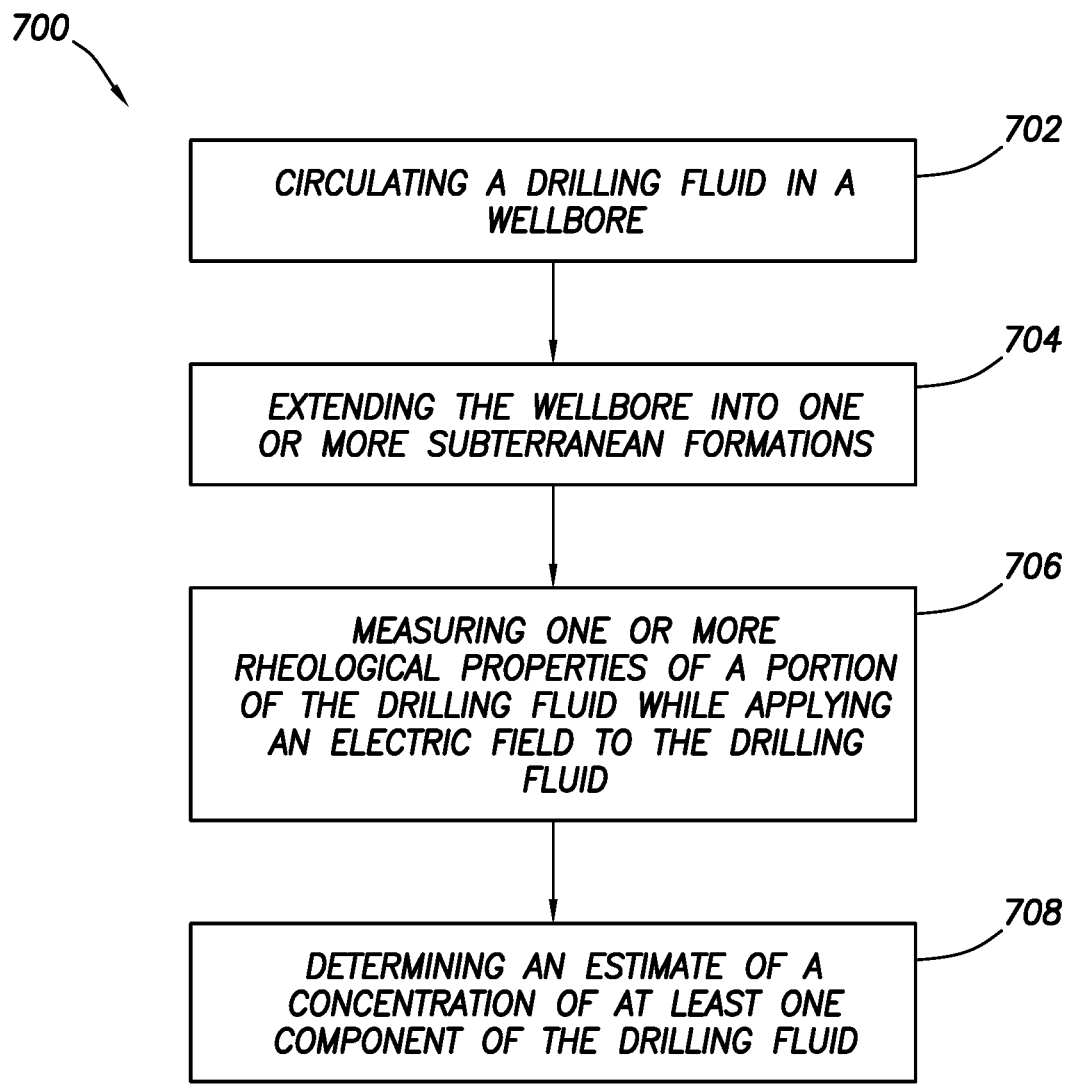
FIG. 7 illustrates a flow chart of an example method for estimating concentration of one or more components in a drilling fluid.

FIG. 7 illustrates a flow chart of a method 700 of drilling that uses electro-rheology in an estimation of a concentration of one or more components in a drilling fluid. At block 702, the method may include circulating a drilling fluid in a wellbore. At block 704, the method may include extending the wellbore into one or more subterranean formations. At block 706, the method may include measuring one or more rheological properties of a portion of the drilling fluid while applying an electric field to the drilling fluid to obtain an electro-rheological profile of the portion of the drilling fluid. At block 708, the method may include determining an estimate of a concentration of at least one component of the drilling fluid based on the electro-rheological profile. The determining the estimate may use a correlation between a rate of change of at least one rheological property as a function of at least one property of the electric field, for example, as described above with respect to FIGS. 1-6. In response to the estimate, remedial action may be taken, for example, an additional quantity of the additive may be added to the drilling fluid.

Figure 8:
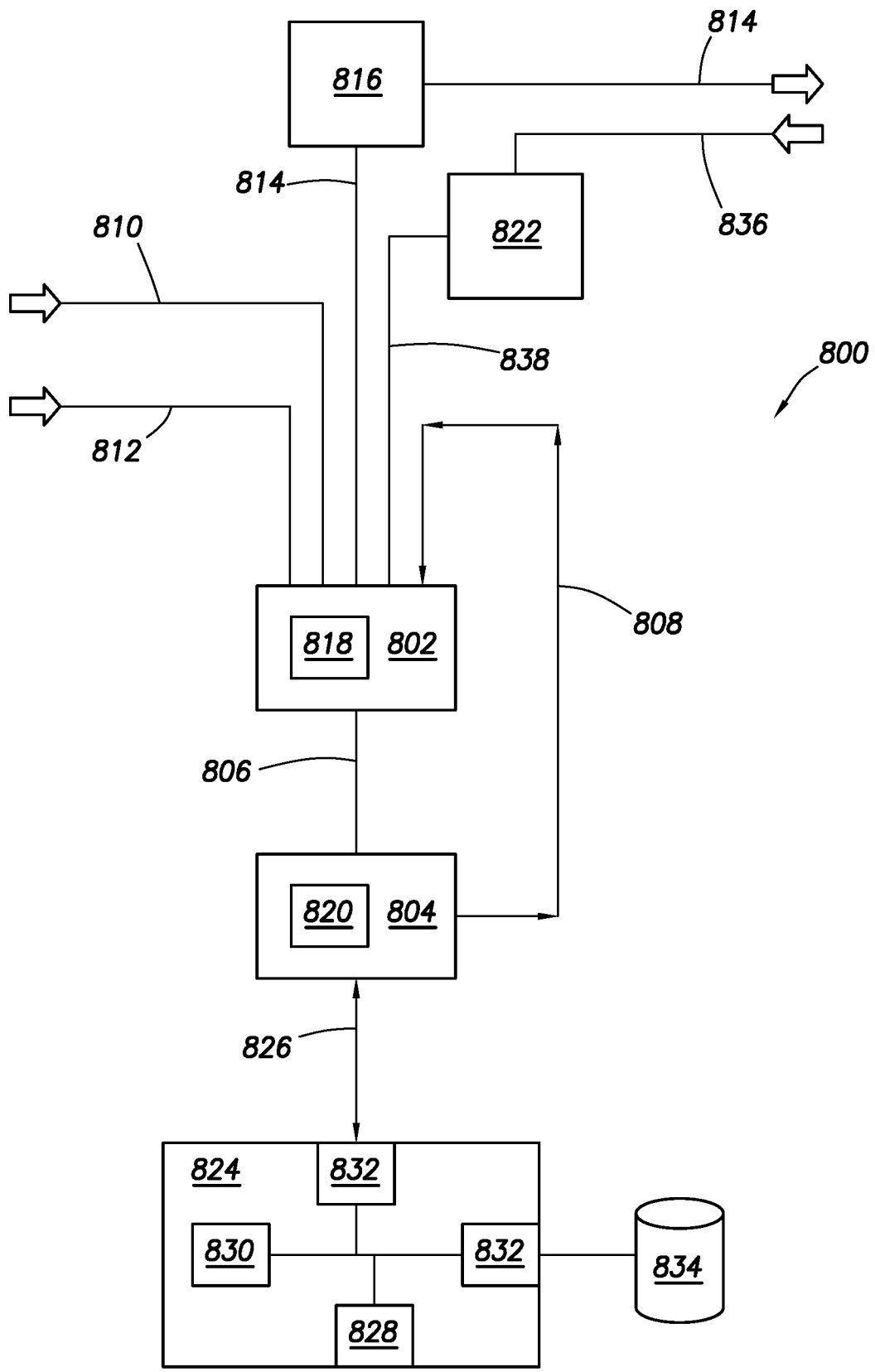
FIG. 8 illustrates a block diagram of a drilling fluid monitoring and handling system.

FIG. 8 illustrates a block diagram of a drilling fluid monitoring and handling system 800 for determining concentration of one or more components of drilling fluids. As illustrated, the fluid monitoring and handling system 800 may generally include a mud pit 802 and a fluid analysis system 804. A portion of the drilling fluid from the mud pit 802 may be fed via a mud pit line 806 to the fluid analysis system 804, which may be configured to perform electro-rheology measurements on the portion of the drilling fluid supplied thereto. The fluid analysis system 804 may analyze the drilling fluid using the example method disclosed above with respect to FIGS. 1-7. After fluid analysis, the portion of the drilling fluid may be returned to mud pit 802 via a return line 808.

The mud pit 802 may be any vessel suitable for holding a drilling fluid. For example, the mud pit 802 may include a container such as a drum or tank, or a series of containers that may or may not be connected. The mud pit 802 may be supplied with the drilling fluid from an initial drilling fluid supply line 810 that provides an initial supply of drilling fluid to the mud pit 802. However, the initial supply of drilling fluid does not imply that the drilling fluid has not been recycled or circulated in a wellbore, but simply indicates that this supply is not presently being circulated or otherwise used in the wellbore.

Drilling fluid additives (e.g., emulsifying agents, clay, viscosifiers, etc.) may be added via a drilling fluid additive supply line 812 to the mud pit 802, if desired, and based on the analysis provided by the fluid analysis system 804. Alternatively or additionally, in an example, the results of the analysis may be used to modify the manufacturing process of the drilling fluid. After the drilling fluid additives have been added to the drilling fluid, the drilling fluid may be retested using the fluid analysis system 804 to verify the drilling fluid was correctly formulated or the drilling fluid may be sent to the wellbore for use in drilling operations via a wellbore line 814 by way of mud pump 816.

The mud pit 802 may include a mixing system 818 to mix the contents of the mud pit 802 as well as any drilling fluid additives. For instance, the mixing system 818 may mix the drilling fluid in the mud pit 802 with drilling fluid from the initial drilling fluid supply line 830, drilling fluid from the return line 8808, drilling fluid additives, additional non-aqueous fluids, aqueous fluids or combinations thereof. In general, the mixing system 818 may be configured to prevent solids within the drilling fluid from settling. The mixing system 818 may use any suitable mixing technique for mixing of the drilling fluid. For instance, the mixing system 818 may include a static mixer, dynamic mixer, or other suitable mixer. The mud pit 802 may further include suitable pumping equipment (not shown) t to pump the drilling fluid in the mud pit 802 to the fluid analysis system 804 via mud pit line 806.

The fluid analysis system 804 may analyze the portion of the drilling fluid in a continuous or non-continuous manner, as desired, and based on whether flow through fluid analysis system 804 is continuous or non-continuous. The fluid analysis system 804 may include one or more instruments 820 for measuring rheology of the drilling fluid while applying an electric field to the drilling fluid. For example, the instrument(s) 820 may include a rheometer and voltage source.

Although the fluid analysis system 804 is shown at the mud pit 802, examples disclosed herein contemplate the placement of fluid analysis system 804 at any point in the fluid monitoring and handling system 800. For example, one or more instruments 820 of the fluid analysis system 804 may alternatively be placed in a fluid reconditioning system 822 (discussed below), the mud pit 802, as well as within the wellbore or in an exit conduit from the wellbore. As such, examples disclosed herein contemplate measuring the rheology while applying an electric field at any point in the drilling fluid handling process, so that the drilling fluid may be monitored and/or subsequently adjusted as desired.

The analysis performed by fluid analysis system 804 may be performed in collaboration with a computer system 824 communicably coupled thereto. As illustrated, the computer system 824 may be an external component of the fluid analysis system 804, however, the computer system 824 may alternatively include an internal component of the fluid analysis system 804, without departing from the scope of the disclosure. The computer system 824 may be connected to the fluid analysis system 804 via a communication link 826. The communication link 826 may include a direct (wired) connection, a private network, a virtual private network, a local area network, a WAN (e.g., an Internet-based communication system), a wireless communication system (e.g., a satellite communication system, telephones), any combination thereof, or any other suitable communication link.

The computer system 824 may be any suitable data processing system including, but not limited to, a computer, a handheld device, or any other suitable device. The computer system 824 may include a processor 828 and a non-transitory computer readable storage medium 830 communicatively coupled to the processor 828. The processor 828 may include one central processing unit or may be distributed across one or more processors in one or more locations. Examples of a non-transitory computer readable storage medium 830 include random-access memory (RAM) devices, read-only memory (ROM) devices, optical devices (e.g., CDs or DVDs), disk drives, and the like. The non-transitory computer readable storage medium 830 may store computer readable program code that may be executed by the processor 828 to process and analyze the measurement data generated by fluid analysis system 804, adjust the parameters of the fluid monitoring and handling system 800, and/or operate a part or whole of the fluid monitoring and handling system 800. Further, from the rheological measurements of the drilling fluid measured by the fluid analysis system 804 while an electric field is applied, the program code may be executed by the processor 828 to determine concentration of one or more drilling fluid additives in the drilling fluid. The concentration may be determined, for example, using a correlation developed using electro-rheology. For example, the concentration may be determined using a correlation between a rate of change of at least one rheological property as a function of at least one property of the electric field as described above with respect to FIGS. 1-6.

The computer system 824 may further include one or more input/output ("I/O") interface(s) 832 communicatively coupled to the processor 828. The I/O interface(s) 832 may be any suitable system for connecting the computer system 832 to a communication link, such as a direct connection, a private network, a virtual private network, a local area network, a wide area network ("WAN"), a wireless communication system, or combinations thereof; a storage device, such as storage 834; an external device, such as a keyboard, a monitor, a printer, a voice recognition device, or a mouse; or any other suitable system. The storage 834 may store data required by the fluid analysis system 804 for performing fluid analysis. For instance, the storage 834 may store a collection of equivalent circuit models that may be used during the EIS analysis. The storage 834 may be or include compact disc drives, floppy drives, hard disks, flash memory, solid-state drives, and the like. Those of ordinary skill in the art will appreciate that suitable data processing systems may include additional, fewer, and/or different components than those described for computer system 824.

Data processing and analysis software native to the fluid analysis system 804 and/or installed on the computer system 824 may be used to analyze the data generated by fluid analysis system 804. This procedure may be automated such that the analysis happens without the need for operator input or control. Further, the operator may select from several previously input parameters or may be able to recall previously measured data. Any of the data may be transferred and/or stored on an external memory device (e.g., a USB drive), if desired.

With continued reference to FIG. 8, the drilling fluid may delivered to a wellbore from mud pit 802 by way of mud pump 816 via wellbore line 814. The mud pump 816 may be any type of pump or pumping system useful for circulating a drilling fluid into a subterranean formation under a sufficient pressure. The drilling fluid that has been circulated within the wellbore may be returned to the mud pit 802 via a circulated drilling fluid return line 836 and provided to a fluid reconditioning system 822 to condition the circulated drilling fluid prior to returning it to the mud pit 802. The fluid reconditioning system 822 may be or include one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid reconditioning system 822 may further include one or more sensors, gauges, pumps, compressors, and the like used to monitor, regulate, and/or recondition the drilling fluid and various additives added thereto. After the drilling fluid has been reconditioned, the drilling fluid may be returned to the mud pit 802 via the reconditioned fluid line.

Figure 9:
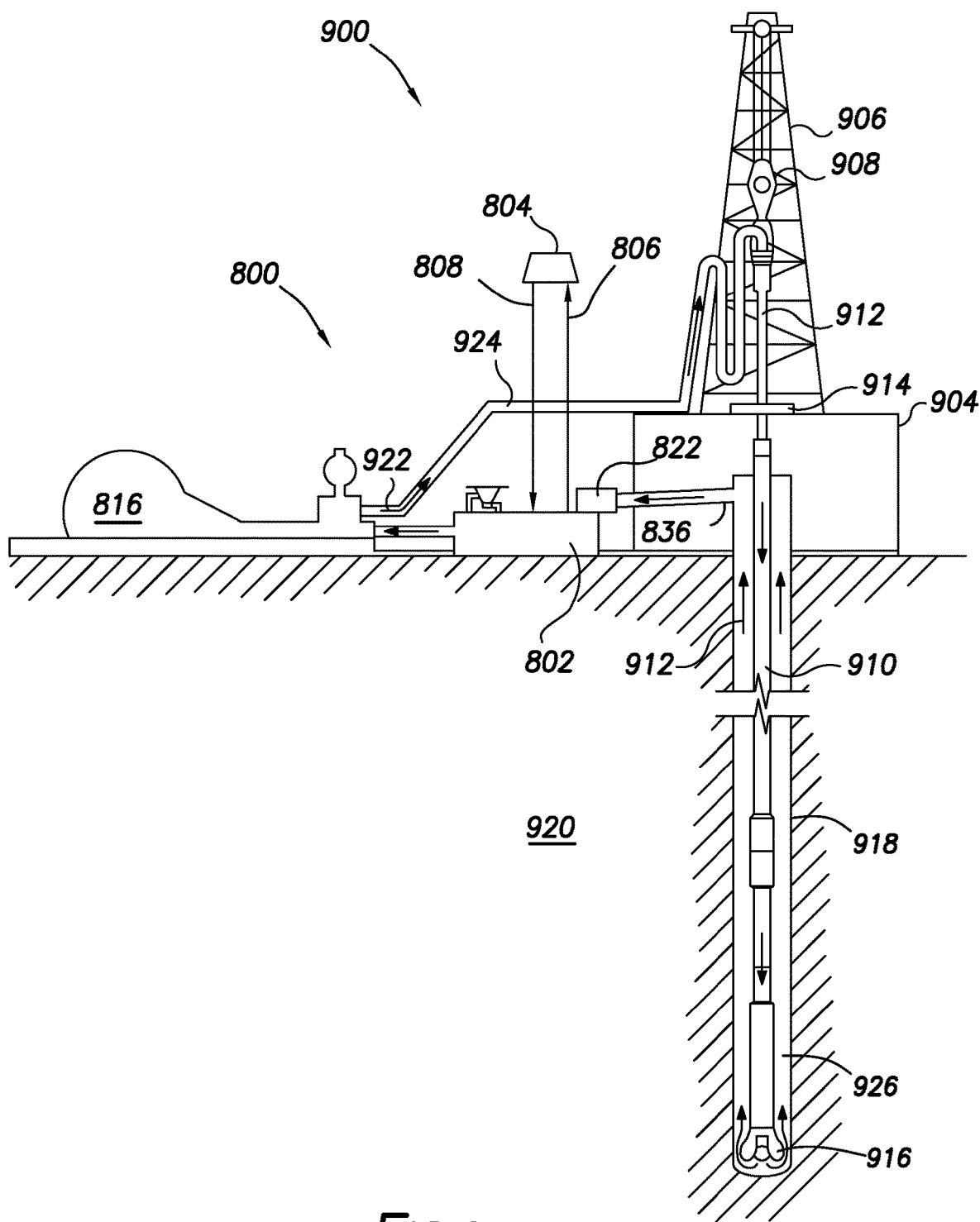
FIG. 9 illustrates an example drilling assembly that incorporates the drilling fluid monitoring and handling system of FIG. 7

FIG. 9 illustrates an example of a drilling system 900 that may employ the fluid monitoring and handling system 800 of FIG. 8 described herein to determine concentration of one or more drilling fluid additives. It should be noted that while FIG. 9 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling assembly 900 may include a drilling platform 904 that supports a derrick 906 having a traveling block 908 for raising and lowering a drill string 910. The drill string 910 may include, but is not limited to, drill pipe and coiled tubing, as generally known to those skilled in the art. A kelly 912 may support the drill string 910 as it may be lowered through a rotary table 914. A drill bit 916 may be attached to the distal end of the drill string 910 and may be driven either by a downhole motor and/or via rotation of the drill string 910 from the well surface. Without limitation, the drill bit 916 may include, roller cone bits, PDC bits, natural diamond bits, any hole openers, reamers, coring bits, and the like. As the drill bit 916 rotates, it may create a wellbore 918 that penetrates various subterranean formations 920.

The drilling assembly 900 may further include the fluid monitoring and handling system 800 as generally described herein. The mud pump 816 of the fluid monitoring and handling system 800 representatively includes any conduits, pipelines, trucks, tubulars, and/or pipes used to fluidically convey the drilling fluid 922 downhole, any pumps, compressors, or motors (e.g., topside or downhole) used to drive the drilling fluid 922 into motion, any valves or related joints used to regulate the pressure or flow rate of the drilling fluid 922, and any sensors (e.g., pressure, temperature, flow rate, etc.), gauges, and/or combinations thereof, and the like.

The mud pump 816 may circulate may circulate the drilling fluid 922 through a feed pipe 924 and to the kelly 912, which conveys the drilling fluid 922 downhole through the interior of the drill string 910 and through one or more orifices in the drill bit 916. The drilling fluid 922 may then be circulated back to the surface via an annulus 926 defined between the drill string 910 and the walls of the wellbore 918. At the surface, the recirculated or spent drilling fluid 922 may be conveyed to the fluid reconditioning system 850 via a circulated drilling fluid return line 836. After passing through the fluid reconditioning system 850, a "cleaned" drilling fluid 922 may be deposited into a nearby mud pit 802. While illustrated as being arranged at the outlet of the wellbore 918 via the annulus 926, those skilled in the art will readily appreciate that the fluid reconditioning system 850 may be arranged at any other location in the drilling assembly 900 to facilitate its proper function, without departing from the scope of the scope of the disclosure.

Referring still to FIG. 9, the fluid monitoring and handling system 800 may further include the fluid analysis system 804, which may be disposed on a skid supported on the drilling platform 904. The fluid analysis system 804 may, for example, continuously or intermittently measure the electro-rheology of the drilling fluid 922. As illustrated, the drilling fluid 922 may be taken from the mud pit 802 via the mud pit line 806 and an analyzed drilling fluid may be returned to the mud pit 802 via the return line 808. Alternatively, the electro-rheology of the drilling fluid 922 may be measured, recorded, and/or analyzed at fluid reconditioning system 822, or at any other suitable location, even while in the wellbore 918 if desired.

Thus, the fluid monitoring and handling system 800 may advantageously monitor the concentration of one or more drilling fluid additives using the example method disclosed herein. The fluid monitoring and handling system 800 may also generate automatic warnings to the personnel when the concentrations deviate from preset safety margins and/or automatically add additional amounts of the one or more drilling fluid additives to the drilling fluid when the concentrations deviate from preset safety margins.

Accordingly, this disclosure describes systems and methods for determining the composition of a drilling fluid using electro-rheology. Without limitation, the systems and methods may further be characterized by one or more of the following statements:

Statement 1: A method for drilling a wellbore including: circulating a drilling fluid in a wellbore; extending the wellbore into one or more subterranean formations; measuring one or more rheological properties of at least a portion of the drilling fluid while applying an electric field to the drilling fluid to obtain an electro-rheological profile of the portion of the drilling fluid; and determining an estimate of a concentration of at least one additive of the drilling fluid based on the electro-rheological profile.

Statement 2: The method of statement 1, wherein the one or more rheological properties include at least one property selected from the group consisting of storage modulus, loss modulus, viscosity, yield stress, and combinations thereof.

Statement 3: The method of statement 1 or statement 2, wherein the applying the electric field includes applying a direct current voltage that increases or decreases as a function of time.

Statement 4: The method of any preceding statement, wherein the electro-rheological profile includes at least one of the one or more rheological properties of the drilling fluid as a function of one or properties of the electric field.

Statement 5: The method of any preceding statement, wherein the electro-rheological profile includes a rate of change of at least one rheological property as a function of at least one property of the electric field.

Statement 6: The method of any preceding statement, wherein the determining the estimate includes applying the rate of change to a correlation between the rate of change of at least one rheological property as a function of at least one property of the electric field for a plurality of sample drilling fluids and a concentration of the additive in the plurality of sample drilling fluids.

Statement 7: The method of any preceding statement, wherein the electro-rheological profile includes a rate of change of storage modulus as a function of voltage of the electric field.

Statement 8: The method of any preceding statement, wherein the at least one additive includes at least one electro-responsive additive selected from the group consisting of an emulsifying surfactant, a clay, and combinations thereof.

Statement 9: The method of any preceding statement, wherein the drilling fluid includes an invert emulsion, wherein the applying the electric field including applying a direct current voltage that increases as a function of time, wherein the electro-rheological profile includes a rate of change of storage modulus as a function of voltage of the electric field, wherein the at least one additive include an emulsifying surfactant; and wherein the determining the estimate includes applying the rate of change to a correlation between the rate of change of the storage modulus as a function of voltage for a plurality of sample drilling fluids and a concentration of the emulsifying surfactant in the plurality of sample drilling fluids.

Statement 10: The method of any preceding statement, further including determining a type of hydrocarbon liquid present in the drilling fluid based on the electro-rheological profile.

Statement 11: A method of using electro-rheology in determining drilling fluid properties, the method including: providing a plurality of sample drilling fluids, wherein each of the sample drilling fluids includes a hydrocarbon liquid, an aqueous liquid, and an additive, wherein a concentration of the additive varies in each of the sample drilling fluids; measuring one or more rheological properties of the plurality of sample drilling fluids while applying an electric field to the drilling fluid to obtain an electro-rheological profile for each of the sample drilling fluids; determining a rate of change of at least one rheological property of the electro-rheological profile as a function of at least property of the electric field for each of the sample drilling fluids; determining a correlation between the rate of change of the at least one property and the concentration of the additive in the sample drilling fluids; measuring one or more rheological properties of at least a portion of an additional drilling fluid while applying an electric field to the drilling fluid to obtain an electro-rheological profile of the additional drilling fluid, wherein the additional drilling fluid including the hydrocarbon liquid, the aqueous liquid, and the additive; and determining a concentration of the additive in the additional drilling fluid based on the correlation.

Statement 12: The method of statement 11, wherein the sample drilling fluids and the additional drilling fluids each individually include an invert emulsion.

Statement 13: The method of statement 11 or statement 12, wherein the at least one rheological property includes at least one property selected from the group consisting of storage modulus, loss modulus, viscosity, yield stress, and combinations thereof.

Statement 14: The method of any one of statements 11 to 13, wherein the applying the electric field in the measuring the one or more rheological properties of the plurality of sample drilling fluids and in the measuring one or more rheological properties of the additional fluids each include a direct current voltage that increases or decreases as a function of time.

Statement 15: The method of any one of statements 11 to 14, wherein the electro-rheological profile includes a rheological property of the drilling fluid as a function of one or properties of the electric field.

Statement 16: The method of any one of statements 11 to 15, wherein the electro-rheological profile includes a rate of change of at least one rheological property as a function of at least one property of the electric field.

Statement 17: The method of any one of statements 11 to 16, wherein the electro-rheological profile of each of the plurality of drilling fluids and the additional drilling fluid includes a rate of change of storage modulus as a function of voltage of the electric field.

Statement 18: The method of any one of statements 11 to 17, wherein the at least one additive includes at least one electro-responsive additive selected from the group consisting of an emulsifying surfactant, a clay, and combinations thereof.

Statement 19: A drilling system including: a drill string; a drill bit attached to a distal end of the drill string; a fluid monitoring and handling system including a mud pit operable to receive a drilling fluid from a wellbore; a mud pump operable to circulate the drilling fluid; and a fluid analysis system including a rheometer and a computer system, wherein the computer system includes a processor and a non-transitory computer readable storage medium that when executed by the processor causes the computer system to determine an estimate of a concentration of at least one additive of the drilling fluid based on an electro-rheological profile of at least a portion of the portion of the drilling fluid.

Statement 20: The drilling system of statement 19, wherein the electro-rheological profile includes a rate of change of at least one rheological property as a function of at least one property of an electric field, and wherein the estimate of the concentration is determined by applying the rate of change to a correlation between the rate of change of the at least one rheological property as a function of the at least one property of the electric field for a plurality of sample drilling fluids and a concentration of the additive in the plurality of sample drilling fluids.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method for drilling a wellbore comprising:
   circulating a drilling fluid in a wellbore;
   extending the wellbore into one or more subterranean formations;
   measuring one or more rheological properties of at least a portion of the drilling fluid while applying an electric field to the drilling fluid to obtain an electro-rheological profile of the portion of the drilling fluid; and
   determining an estimate of a concentration of at least one additive of the drilling fluid based on the electro-rheological profile,
   wherein the electro-rheological profile comprises a rate of change of at least one rheological property as a function of at least one property of the electric field.

2. The method of claim 1, wherein the one or more rheological properties comprise at least one property selected from the group consisting of storage modulus, loss modulus, viscosity, yield stress, and combinations thereof.

3. The method of claim 1, wherein the applying the electric field comprises applying a direct current voltage that increases or decreases as a function of time.

4. The method of claim 1, wherein the electro-rheological profile comprises at least one of the one or more rheological properties of the drilling fluid as a function of one or properties of the electric field.

5. The method of claim 1, wherein the determining the estimate comprises applying the rate of change to a correlation between the rate of change of at least one rheological property as a function of at least one property of the electric field for a plurality of sample drilling fluids and a concentration of the additive in the plurality of sample drilling fluids.

6. The method of claim 1, wherein the electro-rheological profile comprises a rate of change of storage modulus as a function of voltage of the electric field.

7. The method of claim 1, wherein the at least one additive comprises at least one electro-responsive additive selected from the group consisting of an emulsifying surfactant, a clay, and combinations thereof.

8. The method of claim 1:
   wherein the drilling fluid comprises an invert emulsion;

wherein the applying the electric field comprising applying a direct current voltage that increases as a function of time;
wherein the electro-rheological profile comprises a rate of change of storage modulus as a function of voltage of the electric field;
wherein the at least one additive comprise an emulsifying surfactant; and
wherein the determining the estimate comprises applying the rate of change to a correlation between the rate of change of the storage modulus as a function of voltage for a plurality of sample drilling fluids and a concentration of the emulsifying surfactant in the plurality of sample drilling fluids.

9. The method of claim 1, further comprising determining a type of hydrocarbon liquid present in the drilling fluid based on the electro-rheological profile.

10. A method of using electro-rheology in determining drilling fluid properties, the method comprising:
provc
iding a plurality of sample drilling fluids, wherein each of the sample drilling fluids comprises a hydrocarbon liquid, an aqueous liquid, and an additive, wherein a concentration of the additive varies in each of the sample drilling fluids;
measuring one or more rheological properties of the plurality of sample drilling fluids while applying an electric field to the drilling fluid to obtain an electro-rheological profile for each of the sample drilling fluids;
determining a rate of change of at least one rheological property of the electro-rheological profile as a function of at least property of the electric field for each of the sample drilling fluids;
determining a correlation between the rate of change of the at least one property and the concentration of the additive in the sample drilling fluids;
measuring one or more rheological properties of at least a portion of an additional drilling fluid while applying an electric field to the drilling fluid to obtain an electro-rheological profile of the additional drilling fluid, wherein the additional drilling fluid comprising the hydrocarbon liquid, the aqueous liquid, and the additive; and
determining a concentration of the additive in the additional drilling fluid based on the correlation.

11. The method of claim 10, wherein the sample drilling fluids and the additional drilling fluids each individually comprise an invert emulsion.

12. The method of claim 10, wherein the at least one rheological property comprises at least one property selected from the group consisting of storage modulus, loss modulus, viscosity, yield stress, and combinations thereof.

13. The method of claim 10, wherein the applying the electric field in the measuring the one or more rheological properties of the plurality of sample drilling fluids and in the measuring one or more rheological properties of the additional fluids each comprise a direct current voltage that increases or decreases as a function of time.

14. The method of claim 10, wherein the electro-rheological profile comprises a rate of change of at least one rheological property of the additional drilling fluid as a function of one or properties of the electric field.

15. The method of claim 10, wherein the electro-rheological profile of each of the plurality of drilling fluids and the additional drilling fluid comprises a rate of change of storage modulus as a function of voltage of the electric field.

16. The method of claim 10, wherein the at least one additive comprises at least one electro-responsive additive selected from the group consisting of an emulsifying surfactant, a clay, and combinations thereof.

17. The method of claim 10, further comprising determining a type of hydrocarbon liquid present in the additional drilling fluid based on the electro-rheological profile.

18. A drilling system comprising:
a drill string;
a drill bit attached to a distal end of the drill string;
a fluid monitoring and handling system comprising
a mud pit operable to receive a drilling fluid from a wellbore;
a mud pump operable to circulate the drilling fluid; and
a fluid analysis system comprising a rheometer and a computer system, wherein the computer system comprises a processor and a non-transitory computer readable storage medium that when executed by the processor causes the computer system to determine an estimate of a concentration of at least one additive of the drilling fluid based on an electro-rheological profile of at least a portion of the portion of the drilling fluid,
wherein the electro-rheological profile comprises a rate of change of at least one rheological property as a function of at least one property of an electric field.

19. The drilling system of claim 18, wherein the estimate of the concentration is determined by applying the rate of change to a correlation between the rate of change of the at least one rheological property as a function of the at least one property of the electric field for a plurality of sample drilling fluids and a concentration of the additive in the plurality of sample drilling fluids.

20. The drilling system of claim 18, wherein the electro-rheological profile comprises a rate of change of storage modulus as a function of voltage of the electric field.

* * * * *